US00PP16129P2

(12) United States Plant Patent
Brotzman

(10) Patent No.: US PP16,129 P2
(45) Date of Patent: Nov. 29, 2005

(54) CHINESE DOGWOOD NAMED 'MADISON'

(50) Latin Name: ***Cornus kousa* var. *chinensis***
Varietal Denomination: Madison

(75) Inventor: Timothy C. Brotzman, Madison, OH (US)

(73) Assignee: Brotzman's Nursery, Inc., Madison, OH (US)

( * ) Notice: Subject to any disclaimer, the term of this patent is extended or adjusted under 35 U.S.C. 154(b) by 160 days.

(21) Appl. No.: 10/463,011

(22) Filed: Jun. 17, 2003

(51) Int. Cl.[7] ..... A01H 5/00
(52) U.S. Cl. ..... Plt./220
(58) Field of Search ..... Plt./220

*Primary Examiner*—Anne Marie Grunberg
*Assistant Examiner*—Annette H Para
(74) *Attorney, Agent, or Firm*—Renner, Otto, Boisselle & Sklar, LLP

(57) ABSTRACT

A Chinese dogwood plant named Madison, a shrubby tree distinguished by the gold and red colors on the leaves in the summer.

3 Drawing Sheets

Latin name of the genus and species including the variety denomination of the plant claimed: The plant claimed relates to a new and distinct variety of Chinese dogwood, botanically known as *Cornus kousa* var. *chinensis*, and known by the cultivar name Madison.

This new cultivar originated in a group of seedlings obtained from Arcola Creek Nursery in Madison, Ohio and grown at Brotzman's Nursery in Madison, Ohio. This new cultivar was noted as distinctive because of the gold and red colors that appeared on the leaves of stems produced in the second flush of growth in summer.

The Madison variety is the only variant of Chinese dogwood of which I am aware that displays these foliage characteristics. There is a Chinese dogwood cultivar, Gold Star (unpatented), with gold variegation, but it develops a yellow central leaf blotch that is present the entire growing season. Another Chinese dogwood cultivar, Temple Jewel (unpatented), has a faint yellow central leaf blotch in the spring, disappearing by summer when the leaf is mature.

The original Madison cultivar, which is 11 years old, is approximately 3 meters tall and 3 meters wide, and is composed of 7 stems. The largest stem is 6 cm. in diameter at a height of 15 cm. above the ground.

The Madison cultivar has been asexually reproduced at Brotzman's Nursery in Madison, Ohio by means of rooted cuttings, grafting and budding, and plants propagated by this method have displayed the unique characteristics of the original plant.

Referring now to the accompanying drawings.

Figure 1:
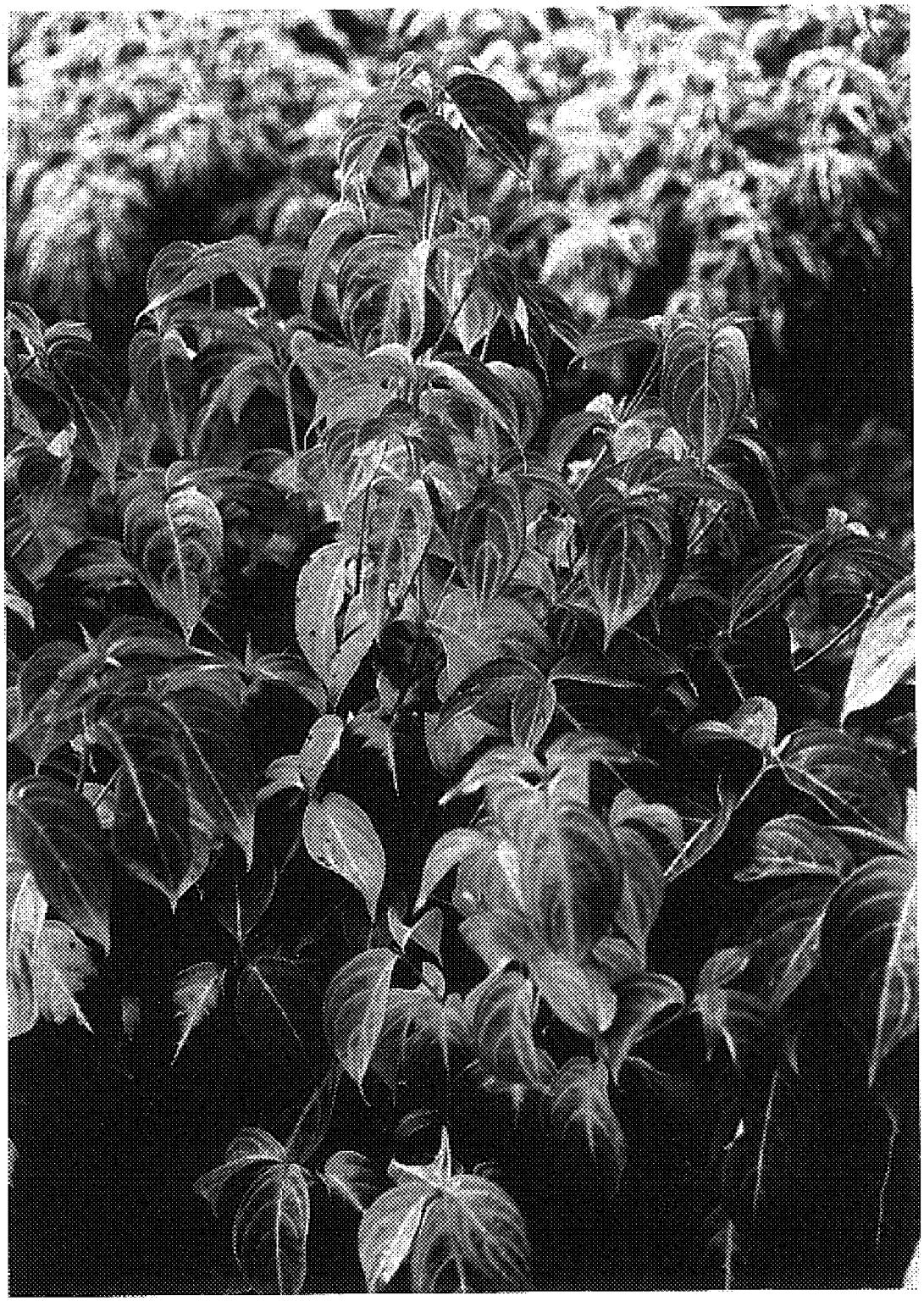
FIG. 1 is a colored photograph illustrating the overall appearance of the cultivar Madison in the summer.
Figure 2:
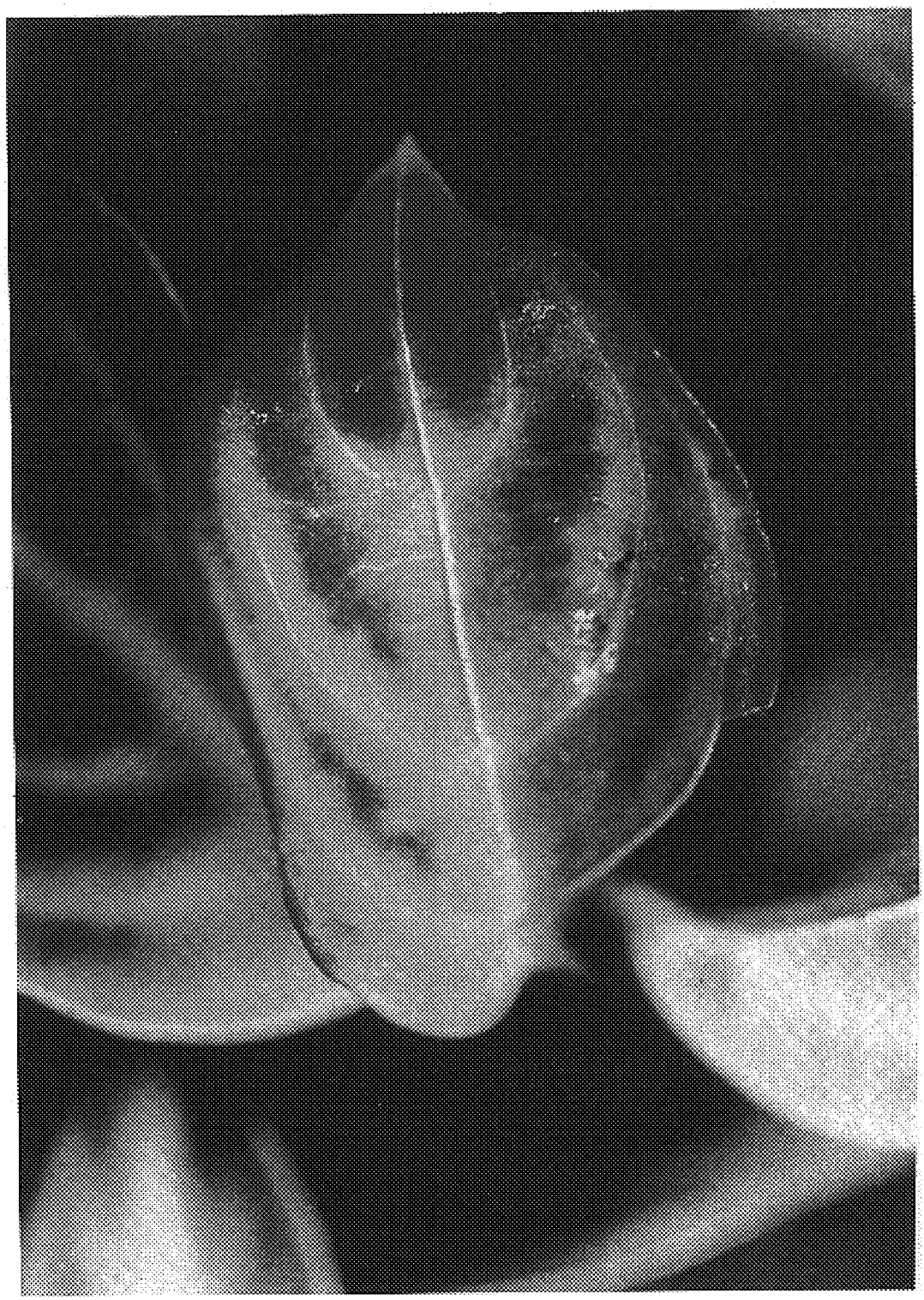
FIG. 2 is a colored photograph illustrating an individual leaf of Madison in the summer.
Figure 3:
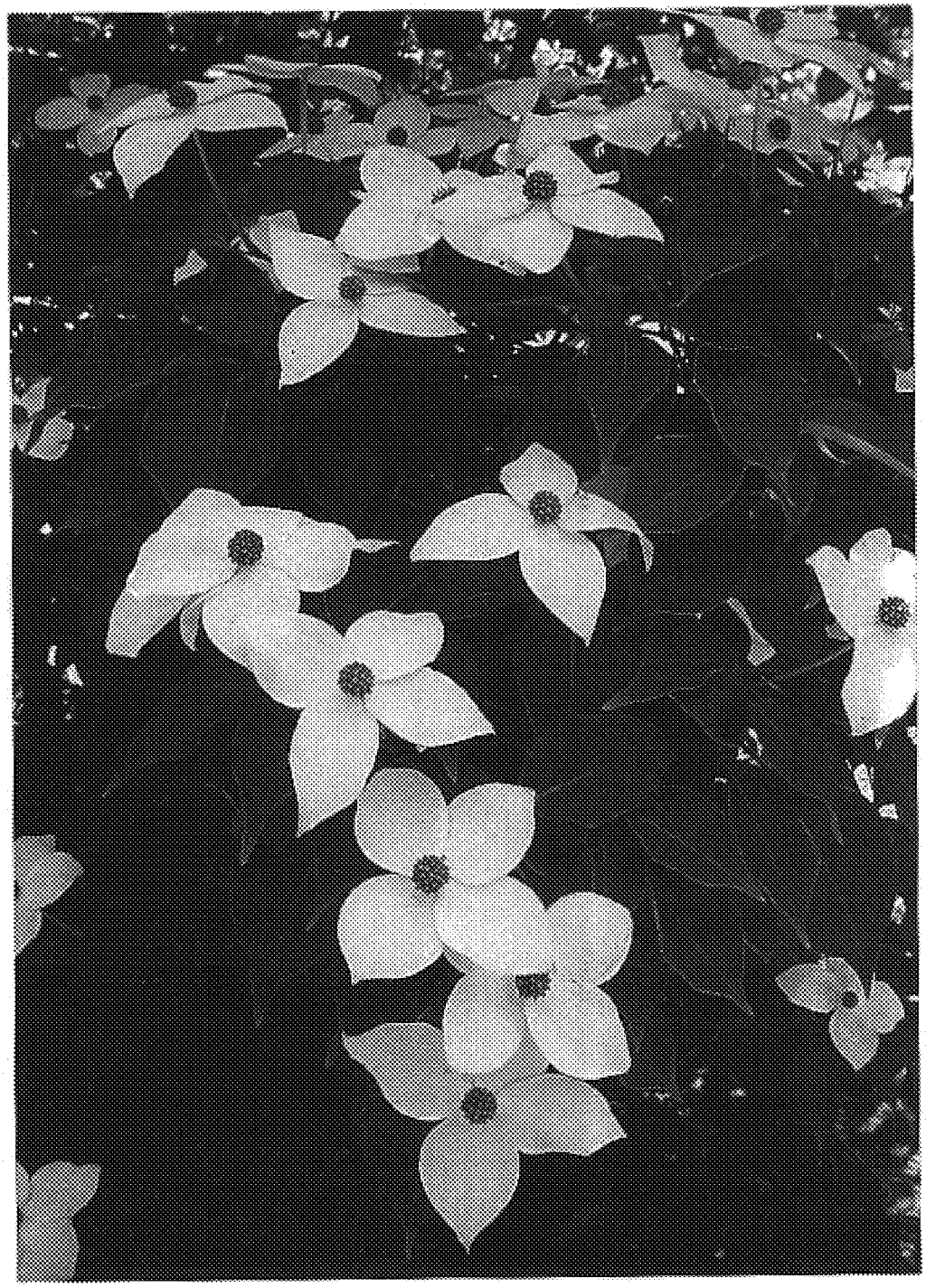
FIG. 3 is a colored photograph depicting the flowers of Madison in the spring.

All three drawing figures show the colors as truly as is reasonably possible to obtain in colored reproductions of this type.

The following is a detailed description of my new cultivar, Madison. In all cases where color is different from the typical and is considered a distinguishing feature of this variety, reference is made to specific colors on the chart issued by The Royal Horticultural Society, London, England. Here follows a detailed description of the characteristics of this cultivar, as displayed by specimens grown at Madison, Lake County, Ohio. Coloration of leaves and bark may be variable, due to conditions of nutrition, stress, age of plant, location on plant and the presence/absence of sun/shade. Plant part comparisons have been made using samples taken from a mature plant where growth rates and characteristics are considered typical.

BOTANICAL DESCRIPTION

Parentage:

*Unknown.*—Obtained as a seedling originating from uncontrolled pollination, growing at Brotzman's Nursery in Madison, Ohio.

Form/size: A shrubby tree 6–10 meters in height and spread at maturity. Vase-shaped as a young plant, becoming rounded, with a layered, horizontal branching habit. A wide range of factors, especially location, age and if the tree is multi-stem or single stem, influences sizes of stems and branches. It is not possible to make a predictable correlation between the diameter of a primary stem and any branch arising from it. However, a primary stem with a diameter of 2.8 cm. was observed to fork (35-degree angle) into two smaller limbs with diameters of 1.5 cm. and 2.2 cm. at a height of 60 cm. above the ground. At similar heights other stems of similar sizes had slightly wider crotch angles averaging 55 degrees, with the widest being 65 degrees. The largest stem of the original Madison cultivar has a diameter of 6 cm. at a height of 15 cm. above the ground.

Hardinaes: Hardy in USDA Hardiness Zone 4b (−25° F.).

Growth rate: Moderate, more rapid in youth.

Stems: Initially smooth and gray. On older trees exfoliating to reveal a patchwork of gray and tan. Whitish lenticles are present on all bark locations, diminishing somewhat on mature surfaces. Bark on lower trunk is of the color gray-green (Grayed-Green Group 197-A), developing gray-orange patchy exfoliation with time (Grayed-Orange Group 165-B).

Branches: New shoots green and purple, turning to gray-orange over time. One year twigs are Grayed-Orange Group 165-A, whereas two year old branches are Grayed-Orange Group 166-A. The final 2.5–10 cm. of the twig, exclusive of terminal buds, may be red (Red Group 46-A)

on the upper side and red-purple (Red-Purple Group 58-A) on the lower side.

Leaves: Deciduous, elliptic-ovate with acuminate tips and cuneate bases, 5–10 cm. long and 2.5–3.5 cm wide. Leaf stalks 6–12 mm. long. Leaf blades glabrous on top, glaucous with scattered tufts of hairs in the leaf axils underneath. Newly emerging leaves in the spring exhibit yellow-green (Yellow-Green Group 144-B), darkening to green (Green Group 141-A). Many leaves of the summer growth flush become gold (Yellow Group 6-B) to varying degrees, beginning in late July to early August in Madison, Ohio. Some leaves are completely gold. In other leaves the base or tip of the leaves is gold. In some leaves the gold color outlines the leaf veins. Additionally, some leaves develop a red coloration (Red Group 45-A) that appears in the areas of the leaf blade between the veins. The red coloration occurs to a lesser extent than the gold. The leaf color remains until it is overwhelmed by the typical red and orange fall colors of the species (Orange-Red Group 33-A). Development of the gold and red leaf coloration appears to be related to the onset of summer heat. If under conditions of drought the summer growth flush does not occur, the gold and red leaf color may be diminished or not appear that year.

Buds:

*Buds are of two types.*—Globose, tapering flower buds averaging 7 mm. in length by 5 mm. in width at the base, color gray-orange (Grayed-Orange Group 177-B); and sharply tapering, triangular vegetated buds averaging 4 mm. in length and 2 mm. in width at the base, color gray-red (Grayed-Red Group 182B).

Flowers: True flowers are greenish and inconspicuous, found in a domed, central umbel approximately 1 cm. wide and 1 cm. high. These flowers are flanked by 4 partially overlapping, tapered, creamy-white bracts, forming a 4-pointed, symmetrical star characterizing each individual inflorescence. Mature bracts most closely resemble Green-White Group 157-A. Bracts average 4.5–5.0 cm. long by 3.5–4.0 cm. wide, thereby producing an inflorescence with an overall width of 9.0–10.5 cm. Flowering commences last week of May to first week of June in Madison, Ohio, lasting about 6 weeks. Depending on general vigor and cultural conditions, the typical floral display is profuse, borne towards the outside of the plant and above the foliage on pedicels averaging 7.0–8.5 cm. in length.

Fruits: The aggregate fruits, as for the species, are pinkish red, globose, and approximately 3 cm. in diameter. They are pendulous, suspended on a 5–6 cm. long stalk.

I claim:

1. A Chinese dogwood plant named Madison, as described and illustrated, a shrubby tree distinguished by the appearance of gold (primary) and red (secondary) coloration on the leaves produced in summer.

* * * * *